US007077569B1

(12) United States Patent
Tybinkowski et al.

(10) Patent No.: US 7,077,569 B1
(45) Date of Patent: *Jul. 18, 2006

(54) APPARATUS AND METHOD FOR SUPPORTING PALLET EXTENDING FROM PATIENT TABLE

(75) Inventors: Andrew P. Tybinkowski, Boxford, MA (US); Robert F. Riemer, Andover, MA (US); Robert M. Williams, Wilmington, MA (US)

(73) Assignee: Analogic Corporation, Peabody, MA (US)

( * ) Notice: Subject to any disclaimer, the term of this patent is extended or adjusted under 35 U.S.C. 154(b) by 309 days.

This patent is subject to a terminal disclaimer.

(21) Appl. No.: 10/732,089

(22) Filed: Dec. 10, 2003

Related U.S. Application Data

(60) Provisional application No. 60/432,349, filed on Dec. 10, 2002.

(51) Int. Cl.
*A61B 6/04* (2006.01)
(52) U.S. Cl. .......................................... 378/209; 5/611
(58) Field of Classification Search ................ 378/209, 378/208; 5/601, 611; 600/415
See application file for complete search history.

(56) References Cited

U.S. PATENT DOCUMENTS

| | | | | |
|---|---|---|---|---|
| 3,158,742 A * | 11/1964 | Morel et al. | ................. | 378/209 |
| 3,818,516 A * | 6/1974 | Hopper et al. | ................. | 5/611 |
| 4,017,737 A * | 4/1977 | Hudson et al. | ................. | 378/39 |
| 4,131,802 A * | 12/1978 | Braden et al. | ................. | 378/20 |
| 4,613,112 A * | 9/1986 | Phlipot et al. | ........... | 251/149.6 |
| 4,685,159 A * | 8/1987 | Oetiker | ........................ | 5/608 |
| 4,914,682 A * | 4/1990 | Blumenthal | ................. | 378/20 |
| 5,034,970 A * | 7/1991 | Yahata et al. | ................. | 378/20 |
| 5,113,420 A * | 5/1992 | Davis et al. | ................. | 378/20 |
| 5,802,638 A * | 9/1998 | Parker et al. | ................. | 5/611 |
| 5,862,549 A * | 1/1999 | Morton et al. | ................. | 5/610 |
| 5,953,776 A * | 9/1999 | Sanders et al. | ................. | 5/611 |
| 6,357,065 B1 * | 3/2002 | Adams | ........................ | 5/618 |
| 6,416,219 B1 * | 7/2002 | Pflaum et al. | ................. | 378/209 |
| 6,637,056 B1 | 10/2003 | Tybinkowski et al. | | |
| 6,675,415 B1 * | 1/2004 | Wong | ........................ | 5/601 |
| 6,776,527 B1 * | 8/2004 | Tybinkowski et al. | ...... | 378/209 |
| 6,929,398 B1 * | 8/2005 | Tybinkowski et al. | ...... | 378/209 |
| 6,955,464 B1 * | 10/2005 | Tybinkowski et al. | ...... | 378/209 |

\* cited by examiner

*Primary Examiner*—Edward J. Glick
*Assistant Examiner*—Thomas R. Artman
(74) *Attorney, Agent, or Firm*—McDermott Will & Emery LLP

(57) ABSTRACT

An apparatus for supporting a pallet extending horizontally from a patient table, including a horizontally extended pallet support for supporting a horizontally extendable pallet of a patient table, and a lifting assembly for vertically supporting the pallet support. The lifting assembly includes a lower base and at least one pair of non-intersecting front and rear lift arms holding the pallet support vertically above the lower base. Each lift arm includes a lower end pivotally connected to the lower base, an upper end pivotally connected to the pallet support, an elbow located between the lower end and the upper end, an elongated lower portion extending between the lower end and the elbow, and an elongated upper portion extending between the elbow to the upper end, with the lower portion and the upper portion connecting at an angle at the elbow.

22 Claims, 3 Drawing Sheets

APPARATUS AND METHOD FOR SUPPORTING PALLET EXTENDING FROM PATIENT TABLE

CROSS-REFERENCE TO RELATED APPLICATION

The present application claims priority from U.S. Provisional Patent Application Ser. No. 60/432,349 filed on Dec. 10, 2002, which is assigned to the assignee of the present application and incorporated herein by reference.

FIELD OF THE INVENTION

The present disclosure relates generally to tomography systems and, more particularly, to a table for supporting a sample, such as a patient, in a tomography scanner during a scanning procedure. Even more particularly, the present disclosure is related to an apparatus and method for supporting a pallet extending horizontally from a patient table.

BACKGROUND OF THE DISCLOSURE

Medical diagnostic imaging and scanning machines such as magnetic resonance imaging (MRI) apparatus, X-ray machines, positron emission tomography (PET) scanners, and computer tomography (CT) scanners are well known. Such machines are quite popular as a tool for diagnosis of tumors and the like. Owing to good quality tomographic images with low dosage X-ray radiation, the CT scanner has become especially well accepted by the medical profession.

An annular gantry normally supports many of the components of a CT scanner and includes an outer ring secured to a stand and an inner ring mounted for rotation within the outer ring. During a scanning procedure, a patient table is positioned through the center of the gantry and the inner ring is rotated about the table. The components supported by the gantry can include an x-ray tube for providing the x-ray beam, one or more high voltage power supplies, balancing weights, a data acquisition module, and a bank of detectors diametrically opposed from the x-ray source. At least some of these components are secured in the inner ring for rotation therewith.

In order to obtain tomographic images of a patient with a CT scanner or X-ray CT apparatus, it is necessary that the patient be located exactly at a predetermined position inside the opening of an annular scan gantry of the apparatus. For this reason, such apparatus has been provided with a patient handling couch or table which is moveable vertically to be in line with an axis of the scan gantry, and moveable horizontally, or axially in and out of the scan gantry. Several patient tables are known for this purpose.

What is desired is a new and improved patient support couch or table apparatus for use with medical diagnostic imaging and scanning machines. In particular, what is desired is a new and improved apparatus and method for supporting a pallet extending horizontally from a patient table.

SUMMARY OF THE DISCLOSURE

The present disclosure provides a new and improved apparatus and method for supporting a pallet extending horizontally from a patient table for positioning a patient within a scanner gantry.

The new and improved apparatus and method of the present disclosure are particularly useful for use with combined tomography scanner (e.g., including a CT scan region on one side and a PET scan region on an opposite side of a gantry of the scanner) having a long gantry. In a combined tomography scanner, images are scanned at two horizontally separated scan regions, and software super-imposes the images. In order to achieve a very accurate, clear image, the position of the patient within the gantry of the combined scanner must not change more than about one (1) millimeter in the vertical direction between the horizontally separated scan regions.

In order to achieve this degree of vertical accuracy between the horizontally separated scan regions, the present disclosure provides a new and improved apparatus and method for supporting a pallet extending horizontally from a patient table for positioning a patient within a gantry of a combined tomography scanner. The patient is transferred to the patient table when the table is in a lowered patient loading position. The table is then vertically raised and mates with a cantilevered pallet support extending horizontally from the apparatus of the present disclosure, and through the gantry bore. Once mated, the table and the apparatus are vertically raised together in a substantially synchronized manner. When vertically aligned with the central axis, or isocenter of the gantry, the pallet and the patient supported thereon are translated horizontally on the pallet support successively through the separated scan regions of the gantry.

According to one aspect of the present disclosure, the pallet of the patient table has a friction plate on a bottom side thereof and is able to slide on top of the rigid pallet support. According to another aspect, the pallet support is made of an x-ray translucent material.

Once the patient has been scanned, the pallet is horizontally retracted back onto the patient table, and both the patient table and the support apparatus are then lowered simultaneously.

According to a further aspect of the present disclosure, a mechanical stop is positioned within the gantry for limiting the vertical lowering of the pallet support. Once the pallet support reaches the mechanical stop, the patient table disengages from the pallet support and the patient table continues being lowered to the patient loading (and unloading) position.

Other features and advantages of the presently disclosed disclosure will become apparent by reference to the following description taken in connection with the accompanying drawings.

BRIEF DESCRIPTION OF THE DRAWINGS

Like reference characters designate identical or corresponding components and units throughout the several views.

DETAILED DESCRIPTION OF EXEMPLARY EMBODIMENTS

Figure 1:
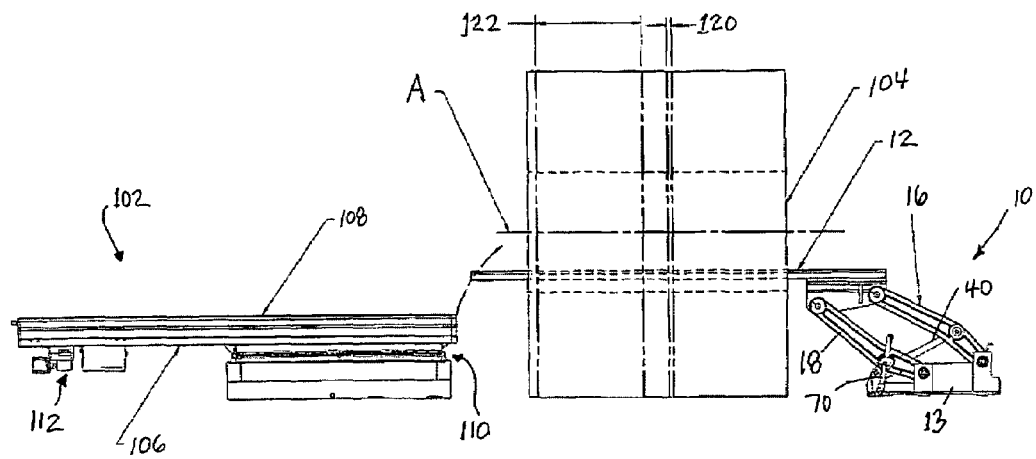
FIG. 1 is a side elevation view of an exemplary embodiment of a new and improved vertically adjustable support apparatus constructed in accordance with the present disclosure for supporting a pallet extending horizontally from a patient table, and wherein the patient table is shown in a vertically lowered position with the extendable pallet retracted, and the support apparatus is shown in a partially raised position with a pallet support extending through the gantry of a combined tomography scanner.
Figure 2:
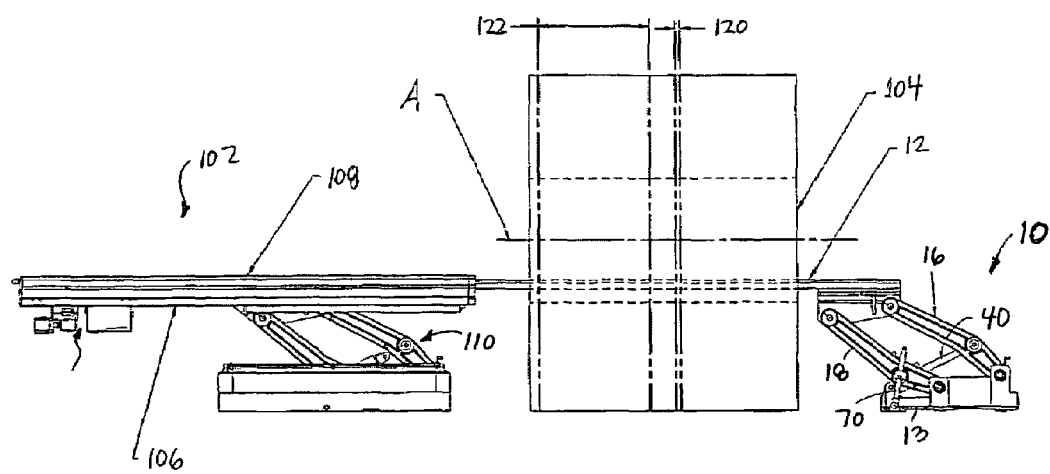
FIG. 2 is a side elevation view showing the patient table of FIG. 1 in a partially raised position, with the extendable pallet still retracted, and in contact, or "mated" with an end of the extended pallet support extending through the gantry of the combined tomography scanner.
Figure 3:
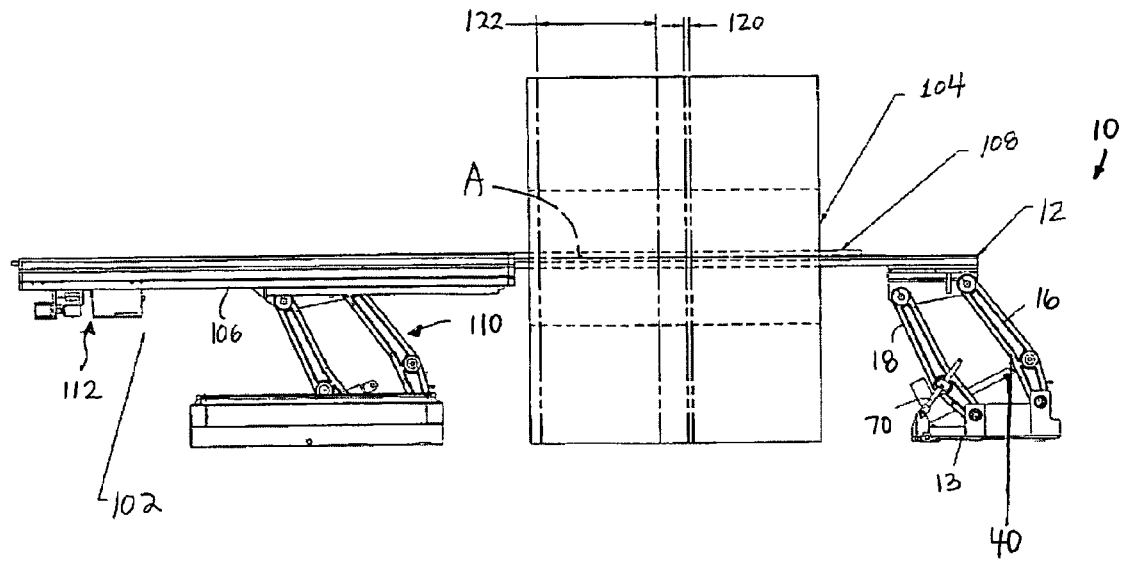
FIG. 3 is a side elevation view of the patient table and the support apparatus of FIG. 1, wherein the table is shown in a raised position with the pallet shown in a horizontally extended position supported by the pallet support of the vertically adjustable support apparatus.

Referring to FIGS. 1 through 3, a patient table 102 for positioning a patient in a gantry 104 of a combined tomography scanner system is shown. An exemplary embodiment of a new and improved apparatus 10 and method for supporting a pallet 108 extending horizontally from the patient table 102 is also shown. The new and improved apparatus 10 and method of the present disclosure are particularly useful for use with a combined tomography scanner including a CT scan region 120 on one side and a PET scan region 122 on an opposite side of the gantry 104. In a combined tomography scanner, images are scanned at the two horizontally separated scan regions 120, 122, and software super-imposes the images. In order to achieve a very accurate, clear image, the position of the patient within the gantry 104 of the combined scanner must not change in a vertical direction more than about one (1) millimeter between the horizontally separated scan regions 120, 122.

The patient table 102 is used to correctly position a patient through the central opening in the gantry 104. After the patient table 102 is correctly positioned with respect to the gantry 104, as shown in FIG. 1, the patient table 102 is operated to lift a patient vertically to a desired position with respect to a rotation axis "A" of the gantry 104 (or central axis or isocenter of the gantry) before beginning a scanning procedure, as shown in FIGS. 2 and 3. During the scanning procedure, the patient table 102 is then operated to move a patient horizontally through the annular gantry 104 in a direction parallel with the rotation axis "A" of the gantry 104, as shown in FIG. 3.

Referring to FIGS. 1 through 3, the patient table 102 includes a lifting assembly or assembly 110, an elongated table assembly 106 supported on the lifting assembly 110, and the elongated pallet 108 positioned on the table assembly 106. As shown, the table 102 is positioned with respect to the gantry 104 such that the elongated pallet 108 extends parallel with the rotation axis "A" of the gantry 104. The elongated pallet 108 is shaped and sized for a patient to lie thereon in alignment with the rotation axis "A" of the gantry 104.

The pallet 108 and the table assembly 106 also include a horizontal drive mechanism 112 for moving the pallet 108 in a horizontal direction on the table assembly 106 parallel with the rotation axis "A" of the gantry 104. In this manner, the pallet 108 can be extended through the opening of the gantry 104 with a patient thereon during a scanning procedure. The table assembly 106, the pallet 108 and the horizontal drive mechanism 112 are described and claimed in detail in co-pending U.S. patent application Ser. No. 10/161,810, filed on Jun. 3, 2002, and entitled HORIZONTAL DRIVE APPARATUS AND METHOD FOR PATIENT TABLE, which is assigned to the assignee of the present application and incorporated herein by reference.

In addition to the horizontal drive apparatus 112, the table 102 includes the lifting assembly 110 supporting the table assembly 106 and the pallet 108. The lifting assembly 110 is used to lift the table assembly 106, the pallet 108 and a patient supported thereon, vertically to a desired position with respect to the rotation axis "A" of the gantry 104 before beginning a scanning procedure. The lifting assembly 110 is described and claimed in detail in co-pending U.S. patent application Ser. No. 10/161,184 filed on Jun. 3, 2002, now U.S. Pat. No. 6,637,056, entitled LIFTING APPARATUS AND METHOD FOR PATIENT TABLE, which is assigned to the assignee of the present application and incorporated herein by reference.

FIGS. 1 through 3 also show an exemplary embodiment of the new and improved vertically adjustable support apparatus 10 constructed in accordance with the present disclosure for supporting the pallet 108 extending horizontally from the patient table 102 for positioning a patient within the gantry 104 of the combined tomography scanner system. In FIG. 1, the patient table 102 is shown in a vertically lowered position with the extendable pallet 108 retracted, and the support apparatus 10 is shown in a partially raised position with a permanently extended pallet support 12 extending through the gantry 104. In FIG. 2, the patient table 102 is shown in a partially raised position, with the extendable pallet 108 still retracted, and in contact, or "mated" with an end of the extended pallet support 12. In FIG. 3, the patient table 102 is shown in a raised position with the pallet 108 horizontally extended into the gantry 104 of the scanning system. The horizontally extended pallet 108 is support by the pallet support 12 of the vertically adjustable support apparatus 10.

The pallet 108 of the patient table 102 can be provided with a friction plate on a bottom side thereof that is able to slide on top of the rigid pallet support 12. In addition, the pallet support 12 can be made of an x-ray translucent material. Furthermore, a mechanical stop can be positioned within the gantry 104 for limiting the vertical lowering of the pallet support 12. Once the pallet support 12 reaches the mechanical stop, the pallet 108 of the patient table 102 disengages from the pallet support 12 and the patient table 102 continues being lowered to the patient loading (and unloading) position.

The vertically adjustable support apparatus 10 also includes a lifting assembly 11 supporting the pallet support 12. The lifting assembly 11 is used to lift the pallet support 12 vertically to a desired position with respect to the rotation axis "A" of the gantry 104 before beginning a scanning procedure. Among other advantages, the lifting assembly 11 provides a combination of both vertical and horizontal movement of the pallet support 12 during operation. The lifting assembly 11 also nests in its lowered position in order to minimize the overall height of the support apparatus 10 when lowered.

The lifting assembly 11 includes a lower base 13, an upper base 14 secured to the pallet support 12, and at least one pair of non-intersecting front and rear lift arms 16, 18 holding the upper base 14 and the pallet support 12 above the lower base 13. In the exemplary embodiment shown in the figures, the lifting assembly 11 is provided with two of the pairs of non-intersecting front and rear lift arms 16, 18 holding the upper base 14 and the pallet support 12 above the lower base 13. The two pairs of arms 16, 18 are positioned side-by-side. However, it should be understood that the lifting assembly 11 of the present invention can include a single pair of the lifting arms 16, 18, or more than two pairs of the lifting arms 16, 18, as desired. To simplify the description of the lifting assembly 11 only one of the two identical pairs of lift arms 16, 18 are described, but the description applies equally to either pair.

Figure 4:
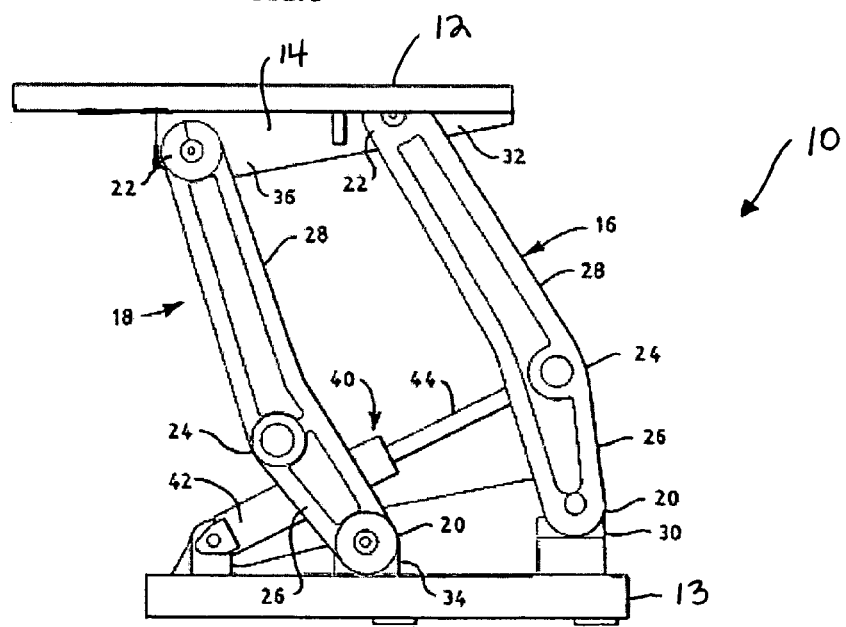
FIG. 4 is an enlarged side elevation view of a lifting assembly, shown in a fully raised position, of the vertically adjustable support apparatus of FIGS. 1 through 3.

As shown best in FIG. 4, the front lift arm 16 and the rear lift arm 18 are identical and each includes a lower end 20 pivotally connected to the lower base 13, an upper end 22 pivotally connected to the upper base 14, and an elbow 24 located between the lower end 20 and the upper end 22. An elongated lower portion 26 extends between the lower end 20 and the elbow 24, and an elongated upper portion 28 extends from the elbow 24 to the upper end 22. The lower portion 26 and the upper portion 28 of each arm 16, 18 connect at an angle at the elbow 24 of the arm (such that each arm somewhat resembles a boomerang).

In the exemplary embodiment shown, the upper portions 28 of the lift arms 16, 18 are longer than the lower portions 26. In addition, the pair of lift arms 16, 18 is mounted such that crocks of the elbows 24 of the lift arms 16, 18 face towards one another, i.e., the two arms 16, 18 are inverted.

The front lift arm 16 is pivotally connected to the lower base 13 at a front bearing 30 of the lower base 13, and pivotally connected to the upper base 14 at a front bearing 32 of the upper base 14. The rear lift arm 18 is pivotally connected to the lower base 13 at a rear bearing 34 of the lower base 13, and pivotally connected to the upper base 14 at a rear bearing 36 of the upper base 14. In the exemplary embodiment shown, the front bearing 30 of the lower base 13 extends further above the lower base 13 than the rear bearing 34 of the lower base 13. In addition, the rear bearing 36 of the upper base 14 extends further below the upper base 14 than the front bearing 32 of the upper base 14. In this manner the front lift arm 16 is mounted higher above the lower base 13 than the rear lift arm 18. In the exemplary embodiment shown, a distance between the front and the rear bearings 30, 34 of the lower base 13 is substantially equal to a distance between the front and the rear bearings 32, 36 of the upper base 14, such that the lower ends 20 and the upper ends 22 of the lift arms 16, 18 are equally spaced apart.

A driving mechanism 40 is pivotally mounted between the elbow 24 of the front lift arm 16 and the lower base 13 for moving the pair of lift arms 16, 18 and causing the lift arms to raise and lower the pallet support 12. The driving mechanism 40 may comprise a hydraulic cylinder mechanism, a ball screw mechanism, or an electromechanical actuator, or the like. In the embodiment shown, the driving mechanism 40 comprises a hydraulic cylinder 42 pivotally connected to the lower base 13 and having an extendable piston 44 pivotally connected to the elbow 24 of the front lift arm 16. A hydraulic manifold and pump assembly 46 is mounted on the lower base 13 and connected to the hydraulic cylinder 42 to provide the hydraulic force for extending the piston 44 and lifting the assembly. During operation, the hydraulic cylinder 42 can be controlled in synchronization with a hydraulic cylinder of the patient table 102 so that the patient table 102 and the support apparatus 10 can be raised and lowered in unison. Although not shown, the vertically adjustable support apparatus 10 can be provided without its own motor for raising and lowering the lift arms 16, 18, and can simply attach to and rely on the patient table 102 for causing the support apparatus 10 to be raised and lowered.

The support apparatus 10 also includes a manual jack assembly 70 for allowing manual operation of the lifting assembly 11 upon a loss of power (loss of hydraulic or electrical power). The jack assembly 70 includes a bearing 72 rotably secured to one of the lift arms 16, 18 of the lifting assembly 11, and an elongated rod 74 extending through the bearing 72 to a proximal end pivotally mounted to the lower base 13. Pivotal movement of the elongated rod 74, therefore, causes the lifting assembly 11 to be raised or lowered.

Figure 5:
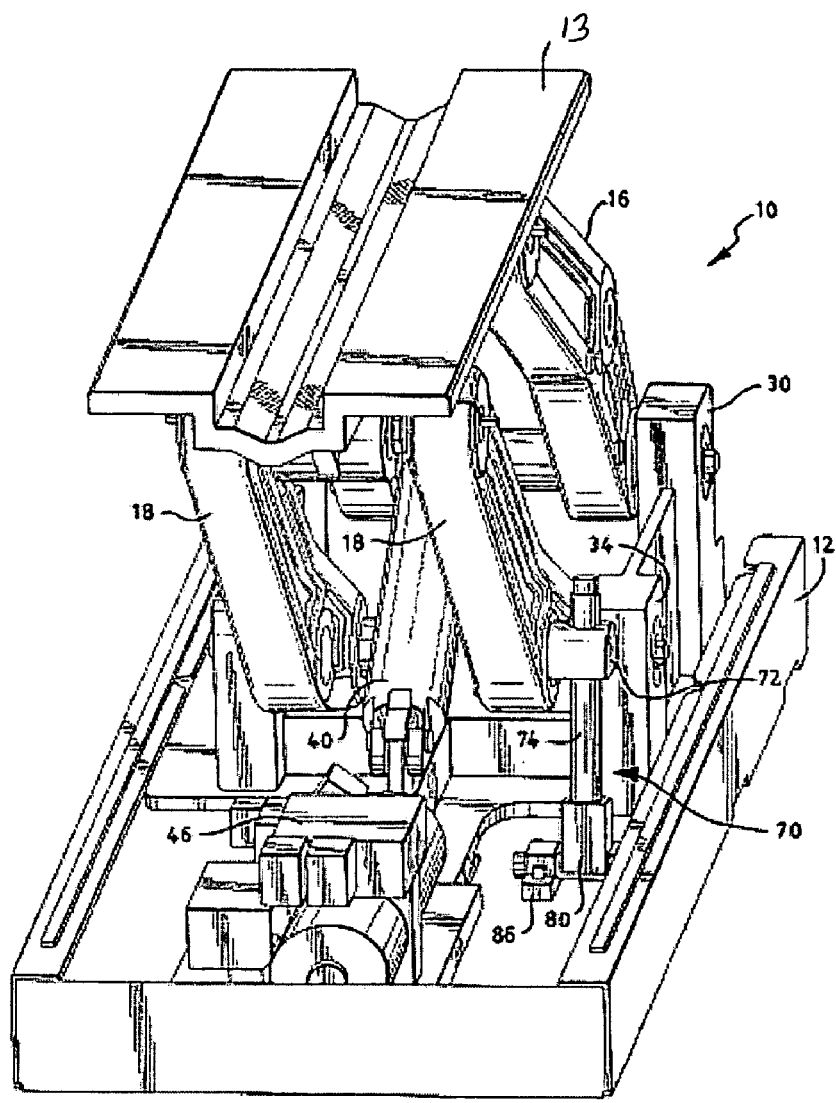
FIG. 5 is a top and end perspective view of the lifting assembly of the support apparatus of FIGS. 1 through 3, further including an exemplary embodiment of a manual jack assembly constructed in accordance with the present invention for allowing manual operation of the lifting assembly upon a loss of power.
Figure 6:
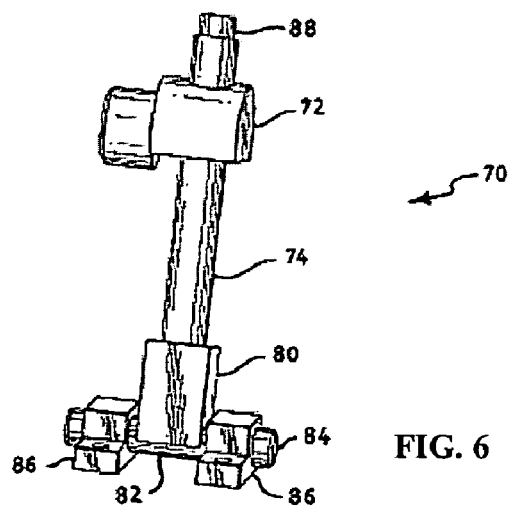
FIG. 6 is a top and end perspective view of the manual jack assembly of FIG. 5.

In the exemplary embodiment shown in FIGS. 5 and 6, the elongated rod 74 of the jack assembly 70 is threaded and extends through a threaded nut secured within the bearing 72, such that the lifting assembly 11 can be raised and lowered by turning the rod 74. The bearing 72 is rotatably mounted in the elbow 24 of the rear lift arm 18 of one of the pairs of lift arms.

In the exemplary embodiment shown, the proximal end of the rod 74 is rotatably received in a bushing 78 of a socket 80. The socket 80 in turn is secured to a sleeve 82 rotatably received on an axle 84 secured to the lower base 13 of the lifting assembly 11 through two mounting blocks 86, to allow pivotal movement of the rod 74 on the lower base 13. A distal end of the rod 74 is shaped to accommodate a hand tool for turning the rod 74. In the embodiment shown, the distal end is provided with a hex head 88, for receiving a wrench for example, such that an operator can raise and lower the lifting assembly 11 using a wrench should electric or hydraulic power be lost.

Although not shown, a cover assembly covering the vertically adjustable support apparatus 10 can be provided. Such a cover assembly may include a collapsible bellows able to collapse when the support apparatus 10 is lowered and expand when the support apparatus 10 is raised.

While the patient table 102 and the support apparatus 10 of the present disclosures are described and shown as being used with an x-ray tomography machine 104, the disclosures can also be used in other applications.

It should be understood that the embodiments of the present disclosure described herein are merely exemplary and that a person skilled in the art may make variations and modifications to the embodiments described without departing from the spirit and scope of the present disclosures. Because certain changes may be made to the above-described support apparatus 10 without departing from the spirit and scope of the present disclosure, all matter contained in the above description or shown in the accompanying drawings shall be interpreted in an illustrative and not a limiting sense. All such equivalent variations and modifications are intended to be included within the scope of this disclosure as defined by the appended claims.

What is claimed is:

1. An apparatus for supporting a pallet extending horizontally from a patient table, comprising:
   a pallet support for supporting a horizontally extendable pallet of a patient table; and
   a lifting assembly for vertically supporting the pallet support, including,
      a lower base;
      at least one pair of non-intersecting front and rear lift arms holding the pallet support vertically above the lower base, wherein each lift arm includes,
         a lower end pivotally connected to the lower base,
         an upper end pivotally connected to the pallet support,
         an elbow located between the lower end and the upper end, and an elongated lower portion extending between the lower end and the elbow, and an elongated upper portion extending between the elbow to the upper end, with the lower portion and the upper portion connecting at an angle at the elbow; and a driving mechanism pivotally mounted between at least one of the lift arms and one of the upper base and the pallet support, wherein the driving mechanism comprises an electromechanical actuator.

2. An apparatus according to claim 1, including two of the pairs of non-intersecting front and rear lift arms positioned side-by-side.

3. An apparatus according to claim 1, wherein the front and the rear lift arms are identical.

4. An apparatus according to claim 1, wherein the upper portions of the lift arms are longer than the lower portions.

5. An apparatus according to claim 1, wherein the front and the rear lift arms are mounted such that crocks of the elbows of the lift arms face towards one another.

6. An apparatus according to claim 1, wherein:

the front lift arm is pivotally connected to the lower base at a front bearing of the lower base, and pivotally connected to the pallet support at a front bearing connected to the pallet support;

the rear lift arm is pivotally connected to the lower base at a rear bearing of the lower base, and pivotally connected to the pallet support at a rear bearing connected to the pallet support;

the front bearing of the lower base extends further above the lower base than the rear bearing of the lower base; and the rear bearing of the pallet support extends further below the pallet support than the front bearing of the pallet support.

7. An apparatus according to claim 6, wherein a distance between the front and the rear bearings of the lower base is substantially equal to a distance between the front and the rear bearings of the pallet support.

8. An apparatus according to claim 1, wherein the driving mechanism is pivotally connected between the elbow of the front lift arm and the lower base.

9. An apparatus according to claim 1, further including a cover assembly covering the lifting assembly.

10. An apparatus according to claim 1, further comprising a jack assembly comprising:

a bearing rotably secured to one of the lift arms of the lifting assembly; and an elongated rod extending through the bearing to a proximal end pivotally mounted to one of the upper base and the pallet support.

11. An apparatus according to claim 10, wherein the proximal end of the elongated rod is pivotally mounted to the lower base.

12. An apparatus according to claim 10, wherein the bearing is rotatably mounted in the elbow of the rear lift arm.

13. An apparatus according to claim 1, wherein the pallet support is made of an x-ray translucent material.

14. An x-ray tomography scanner system including the apparatus of claim 1, and further comprising an annular gantry rotatable about a horizontal center of rotation and containing therein an x-ray source for projecting a beam of x-rays across the center of rotation to a detector array on an opposite side of the gantry, and wherein the lifting assembly can be used to support a pallet horizontally extending from a patient table assembly such that a patient lying on the table assembly can be aligned with the center of rotation of the gantry.

15. A system according to claim 14, further comprising a patient table includes a lifting assembly, an elongated table assembly supported on the lifting assembly, and an elongated pallet positioned on the table assembly, wherein the table can be positioned with respect to the gantry such that the elongated pallet extends parallel with the rotation axis of the gantry and can be supported on the pallet support.

16. A system according to claim 15, wherein the table assembly also includes a horizontal drive mechanism for moving the pallet in a horizontal direction on the table assembly parallel with the rotation axis of the gantry so that the pallet can be extended through the opening of the gantry with a patient thereon during a scanning procedure.

17. A system according to claim 15, wherein the pallet of the patient table includes a friction plate on a bottom side thereof for sliding on the pallet support.

18. A system according to claim 14, wherein a mechanical stop is positioned within the gantry for limiting the vertical lowering of the pallet support.

19. An apparatus according to claim 1, further comprising a patient table includes a lifting assembly, an elongated table assembly supported on the lifting assembly, and an elongated pallet positioned on the table assembly, wherein the elongated pallet can be extended horizontally from the table assembly and supported on the pallet support.

20. An apparatus according to claim 19, wherein the table assembly also includes a horizontal drive mechanism for moving the pallet in a horizontal direction on the table assembly so that the pallet can be extended to the pallet support.

21. An x-ray tomography scanner system including:

an apparatus for supporting a pallet extending horizontally from a patient table, comprising:

a pallet support for supporting a horizontally extendable pallet of a patient table; and a lifting assembly for vertically supporting the pallet support, including, a lower base;

at least one pair of non-intersecting front and rear lift arms holding the pallet support vertically above the lower base, wherein each lift arm includes, a lower end pivotally connected to the lower base, an upper end pivotally connected to the pallet support, an elbow located between the lower end and the upper end, and an elongated lower portion extending between the lower end and the elbow, and an elongated upper portion extending between the elbow to the tipper end, with the lower portion and the upper portion connecting at an angle at the elbow;

an annular gantry rotatable about a horizontal center of rotation and containing therein an x-ray source for projecting a beam of x-rays across the center of rotation to a detector array on an opposite side of the gantry, and wherein the lifting assembly can be used to support a pallet horizontally extending from a patient table assembly such that a patient lying on the table assembly can be aligned with the center of rotation of the gantry; and a patient table that includes a lifting assembly, an elongated table assembly supported on the lifting assembly, and an elongated pallet positioned on the table assembly, wherein the table can be positioned with respect to the gantry such that the elongated pallet extends parallel with the rotation axis of the gantry and can be supported on the pallet support, and wherein the lifting assembly of the table includes a lower base, an upper base securable to the table assembly, and at least one pair of non-intersecting front and rear lift arms holding the upper base vertically above the lower base.

22. An apparatus for supporting a pallet extending horizontally from a patient table, the apparatus comprising:
   a pallet support for supporting a horizontally extendable pallet of a patient table; and
   a lifting assembly for vertically supporting the pallet support, including,
      a lower base;
      at least one pair of non-intersecting front and rear lift arms holding the pallet support vertically above the lower base, wherein each lift arm includes,
         a lower end pivotally connected to the lower base,
         an upper end pivotally connected to the pallet support,
         an elbow located between the lower end and the upper end, and
         an elongated lower portion extending between the lower end and the elbow, and
         an elongated upper portion extending between the elbow to the upper end, with the lower portion and the upper portion connecting at an angle at the elbow;
   a patient table includes a lifting assembly, an elongated table assembly supported on the lifting assembly, and an elongated pallet positioned on the table assembly, wherein the elongated pallet can be extended horizontally from the table assembly and supported on the pallet support, and wherein the lifting assembly of the table includes a lower base, an upper base securable to the table assembly, and at least one pair of non-intersecting front and rear lift arms holding the upper base vertically above the lower base.

* * * * *